United States Patent
Klitgaard et al.

Patent Number: 6,110,149
Date of Patent: *Aug. 29, 2000

[54] SYRINGE

[75] Inventors: Christian Peter Klitgaard, Smørum; Steffen Hansen, Hillerød; Gabriel Jørgensen, København K, all of Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/926,050

[22] Filed: Sep. 9, 1997

Related U.S. Application Data
[60] Provisional application No. 60/049,073, Jun. 10, 1997.

[30] Foreign Application Priority Data

Sep. 13, 1996 [DK] Denmark ............................. 0992/96

[51] Int. Cl.⁷ ..................................................... A61M 5/00
[52] U.S. Cl. ......................... 604/209; 604/207; 604/208; 604/211; 604/218
[58] Field of Search ................................ 604/181, 187, 604/218, 220, 209, 210, 116, 117, 131, 207, 208

[56] References Cited

U.S. PATENT DOCUMENTS

| | | | |
|---|---|---|---|
| 4,231,368 | 11/1980 | Becker | 604/117 |
| 4,415,101 | 11/1983 | Shapiro et al. | 604/209 |
| 4,437,859 | 3/1984 | Whitehouse et al. | 604/131 |
| 4,592,745 | 6/1986 | Rex et al. | 604/211 |
| 4,710,178 | 12/1987 | Leonard et al. | |
| 4,959,056 | 9/1990 | Dombrowski et al. | 604/207 |
| 4,973,318 | 11/1990 | Holm et al. | 604/218 |
| 5,226,895 | 7/1993 | Harris | 604/207 |
| 5,238,654 | 8/1993 | Nohl et al. | 604/187 |
| 5,279,585 | 1/1994 | Balkwill | 604/207 |
| 5,478,316 | 12/1995 | Bitdinger et al. | 604/187 |
| 5,722,956 | 3/1998 | Sims et al. | 604/131 |
| 5,725,508 | 3/1998 | Chanoch et al. | 604/207 |

FOREIGN PATENT DOCUMENTS

| | | |
|---|---|---|
| WO 94/12228 | 6/1994 | WIPO . |
| WO 95/09021 | 4/1995 | WIPO . |

*Primary Examiner*—Wynn Wood Coggins
*Assistant Examiner*—Michael M. Thompson
*Attorney, Agent, or Firm*—Steve T. Zelson, Esq.; Reza Green, Esq.

[57] ABSTRACT

The present invention relates to syringes for apportioning set doses from an ampoule has a dose setting and injection mechanism comprising a dose setting member which may be moved in one direction to set a dose and in the opposite direction to inject the set dose. A piston advancing mechanism comprises a piston rod and a piston rod drive, and the dose setting and injection mechanism is coupled to the piston advancing mechanism through a unidirectional coupling transmitting only movement of the dose setting member in the dose injecting direction to the piston rod drive. Operation of an air shot button enables influence on the piston advancing mechanism to advance the piston to expel an adjustable fixed volume. The air shot button is either coupled to the piston rod drive through a unidirectional coupling through which the piston rod is advanced when the air shot button is pressed, or it moves the end stop for an injection button so that this button may be pressed beyond its normal depressed end position.

7 Claims, 2 Drawing Sheets

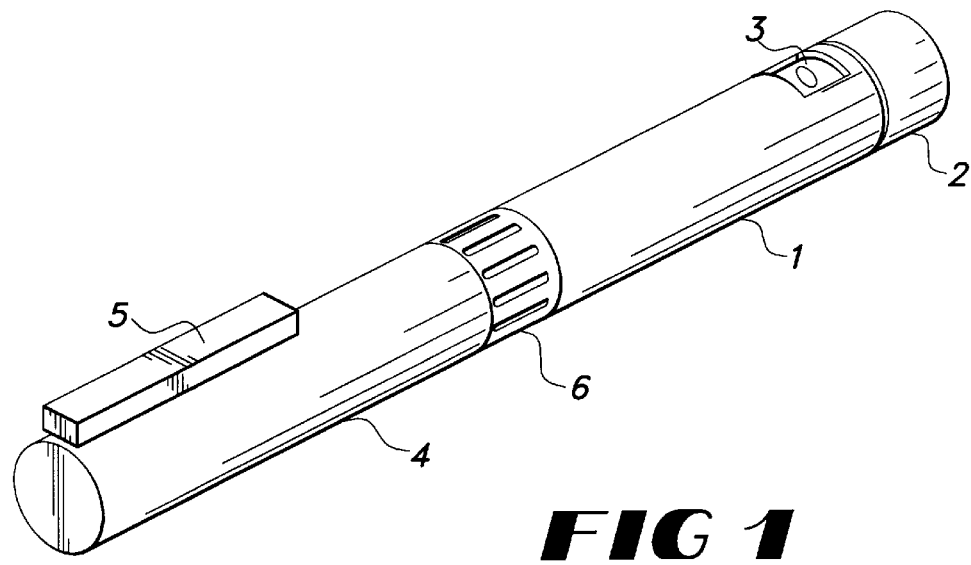
FIG 1
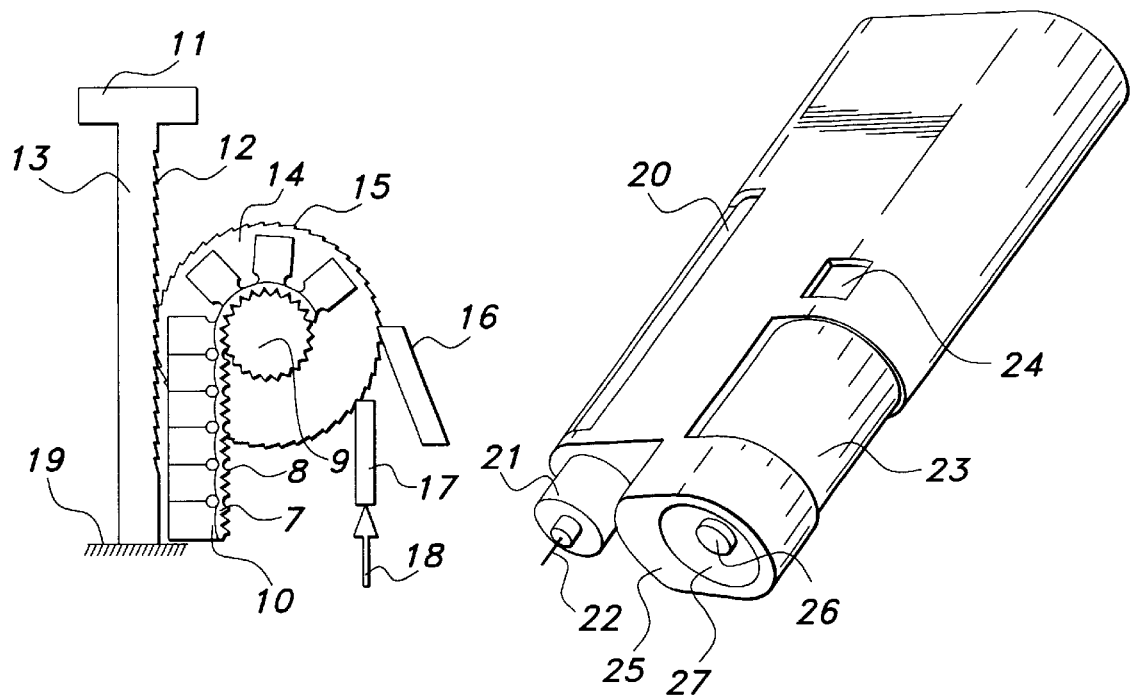
FIG 2   FIG 3

SYRINGE

CROSS-REFERENCE TO RELATED APPLICATIONS

This application claims priority under 35 U.S.C. 119 of Danish application 0992/96 filed Sep. 13, 1996 and U.S. provisional application 60/049,073 filed Jun. 10, 1997, the contents of which are fully incorporated herein by reference.

BACKGROUND OF THE INVENTION

1. Field of the Invention

The invention relates to syringes by which medicine may be apportioned in preset doses from an ampoule, the syringes comprising a dose setting mechanism which is through unidirectional coupling coupled to a piston rod drive mechanism which advances the piston rod into the ampoule so that the dose setting mechanism may be moved in one direction to set a dose without transmission of the movement of the piston rod, and in another direction to inject the set dose, by which the movement is transmitted to the piston rod to advance it a distance causing an amount of medicine corresponding to the set dose to be pressed out of the ampoule.

The medicine is pressed out through a needle which is mounted on the syringe communicating with the inner space of the ampoule. To inject a dose of medicine a dose is set by operation of the dose setting mechanism, the needle is inserted through the skin of the user or patient, and the set dose is injected by operating the dose setting mechanism in the. opposite direction of the direction used by the setting of the dose.

2. Description of the Related Art

EP 37 696 describes a medicine dispensing device wherein a unidirectional coupling between a first drive member and a ratchet-toothed second drive member driving the piston transmits only movement of the first drive member in an piston advancing direction to the second drive member.

WO 93/07922 describes a syringe by which a dose is set by rotating a dose setting knob in one direction. The dose setting knob is connected with a part of an unidirectional coupling through which the dose setting knob is coupled to a piston drive comprising a nut which is so journaled in the housing that it may be rotated but not longitudinally displaced in this housing. An inner thread in the nut engages an outer thread on a piston rod which rod may be displaced longitudinally in the housing but not rotated. The unidirectional coupling between the dose setting knob and the piston drive nut is so directed that only piston advancing rotation is transmitted to the piston drive nut.

However, before the dose is set and made ready for injection it must be ensured that no air is injected. To get rid of possible air in the needle or in the ampoule a small dose of the medicine, e.g. 10 or 20 $\mu$l, is set and an injection operation is made without insertion of the needle into the skin. By this so called air shot air is driven out through the needle. At the point of the needle it can easily be seen if all air has been expelled and only liquid is leaving the needle. If a fine liquid jet is not seen at the end of the air shot a new small dose must be set and a new air shot be made until such a jet is seen.

To avoid to have to perform repetitive settings of a small dose and subsequent air shot the user may feel an impulse to set a somewhat larger dose to make sure that only one air shot has to be made. Thereby unnecessary amounts of expensive medicine may be wasted. Also in many syringes of the kind described no undo mechanism exists so that a dose once set cannot just be annulled, or at least this will demand special precautions. Therefore if a dose is set and the user thereafter remember that he forgot to make an air shot the dose must be wasted or annulling precautions must if possible be taken. Further, during the air shot the syringe must be operated with the needle pointing upward. As most syringes are designed to be operated with the needle pointing mainly downward, operation with the needle pointing upward may be rather awkward.

It is an object of the invention to provide a syringe by which these disadvantages may be avoided.

SUMMARY OF THE INVENTION

This is obtained by a syringe of the kind described in the opening of this specification which syringe according to the invention is characterized in that an air shot button is provided acting only on the piston drive mechanism side of the unidirectional coupling to advance the piston rod by a distance corresponding to expulsion of a fixed volume of medicine. The fixed volume may be set by the manufacturing of the syringe to be of the order 10 to 20 $\mu$l. Alternatively the fixed volume may be adjustable to be set to a preferred fixed dose.

When all air has been expelled from the cartridge and the needle the air shot button may be used for injection of fixed small doses of a size corresponding to the air shot.

The air shot button is coupled to the piston rod through a second unidirectional coupling through which the piston rod is advanced when the air shot button is pressed and which allow the air shot button to return to its initial position without influencing the piston rod when the air shot button is released.

According to an embodiment of the invention the second unidirectional coupling comprises at pawl connected to the air shot button, which pawl engage a toothing on a piston rod drive.

According to another embodiment of the invention the second unidirectional coupling comprises a pawl connected to the air shot button, which pawl engages a toothing on a piston drive nut driving a threaded piston rod.

According to the invention the pawl of the second unidirectional coupling may form a piston retraction detent.

In an embodiment of the invention of the invention the air shot button by operation moves the end stop for an injection button this way enabling influence on the piston advancing mechanism to advance the piston a distance corresponding to expulsion of a fixed volume of medicine which is obtained by pressing of the injection button.

BRIEF DESCRIPTION OF THE FIGURES

In the following the invention is described in further details with references to the drawing, wherein FIG. 1 shows schematically a pen syringe provided with a air shot button in the shape of a rotatable belt which may be rotated to drive a piston advancing nut.

FIG. 2 shows schematically the function of an air shot button in an embodiment of a syringe having a piston drive mechanism based on a toothed rod, FIG. 3 shows schematically a syringe with the piston rod drive mechanism shown in FIG. 2.

DETAILED DESCRIPTION OF THE INVENTION

Figure 4:
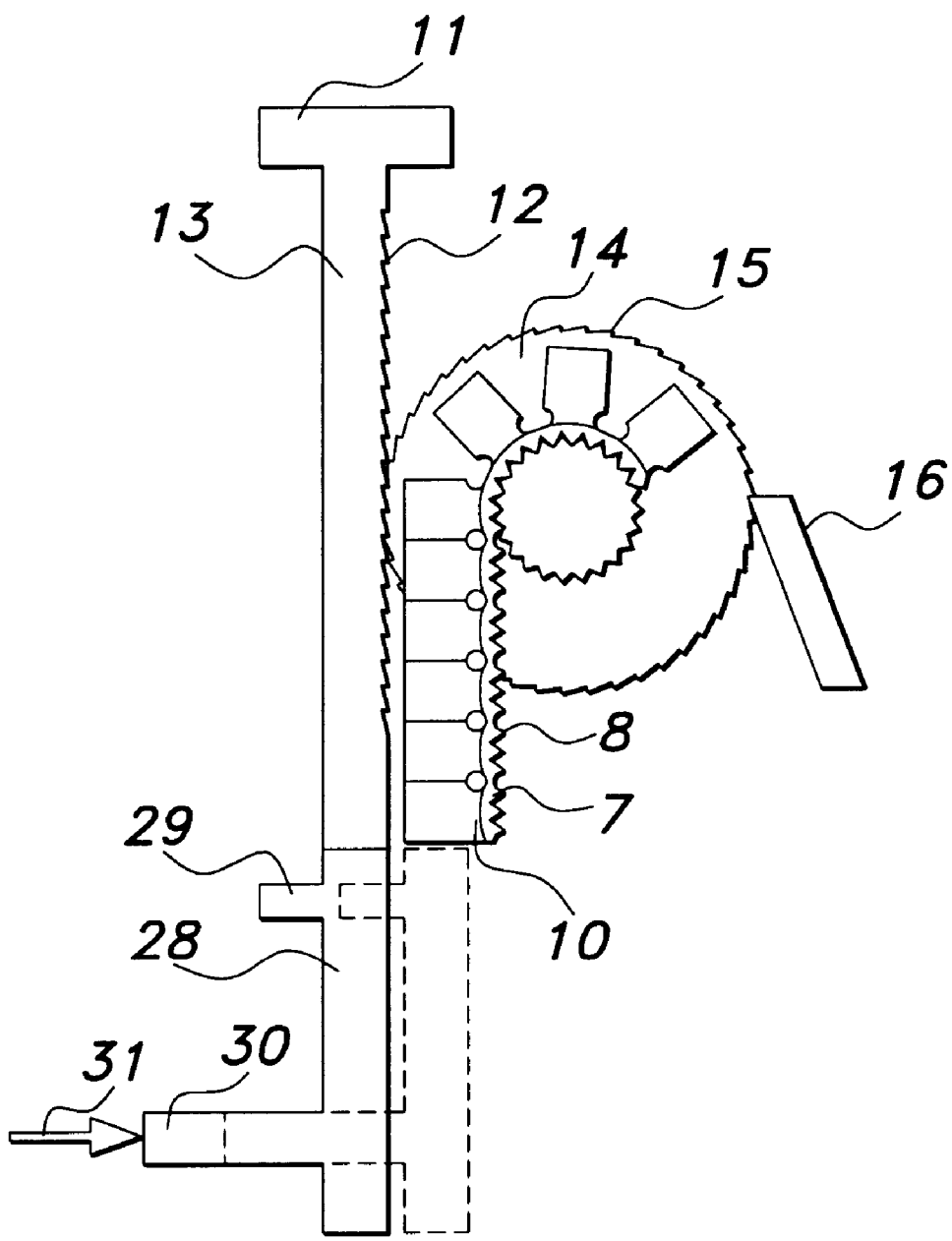
FIG. 4 shows another embodiment of the piston drive mechanism shown in FIG.

FIG. 1 shows schematically a conventional pen shaped syringe comprising a housing 1, a knob 2 for setting of a dose the size of which may be read through a window 3. An end of the syringe which has a needle receiving member is in the figure covered by a cap 4 which is provided with a clip 5 so that the pen may be carried in a pocket like a fountain pen. The piston drive mechanism of the pen is of the type by which a nut is rotatable but not longitudinally displaceable in the housing and through a unidirectional coupling is rotated in a direction by which a threaded piston rod which is not rotatable but longitudinally displaceable in the housing by engagement with the thread of the nut is driven into an ampoule to press out the medicine in this ampoule. An air shot is established by providing the pen with a ring 6 which may be reciprocally rotated and which by an internal pawl engaging a pawl wheel on the nut rotates the piston drive nut a small angle each time by which the piston drive nut is rotated in one direction whereas the pawl rides over the teeth of the pawl wheel when the ring is rotated in the opposite direction.

FIG. 2 shows schematically the piston rod drive mechanism for a pen type which due to the use of a flexible piston rod may be made shorter than a pen but which at the same time is wider as the dose setting mechanism is placed next to the ampoule instead of in extension of it. The piston rod is formed by short sections 7 which have teeth 8 for engagement with a driving gear 9. Further each section has a stiffening plate 10 and the sections are hinged together to make the piston rod flexible. In the part of the piston rod which is pressing the piston in an ampoule the stiffening plates are piled in a way enabling transmission of pressure forces from the gear to the piston through the piled stiffening plates 10. Injection is performed by pressing a button 11 which through a toothing 12 with ramp shaped teeth on a carrier rod 13 transmits a downward movement of this carrier rod 13 to a pawl wheel 14 which is fixed to the gear 9 and has ramp shaped teeth 15 along its periphery. The injection movement is stopped when an end stop 19 is abutted by the end of the carrier rod 13. By setting the dose the carrier rod 13 is moved away from the end stop 19 by which movement the teeth 12 of the carrier 13 will slide over the ramps of the teeth 15 of the pawl wheel 14 as a detent 16 prevents the pawl wheel 14 from rotating in a piston rod withdrawing direction whereas the same detent allows rotation of the pawl wheel 14 in the piston rod advancing direction.

A push rod 17 transmits the movement of a not shown air shot button in the direction indicated by the arrow 18. The rod 17 will rotate the pawl wheel 14 in a piston advancing direction as the teeth on the carrier and the detent 16 allows such a rotation. However, when the push rod 17 is returned it will slide over the ramps of the teeth 15 of the pawl wheel 14 which wheel will be prevented from rotating as well by the abrupt edges of the teeth 12 on the carrier as by the detent 16. In fact the detent 16 may be omitted as the carrier acts as a detent when the air shot button is operated and the push rod may act as a detent when the carrier is operated.

FIG. 3 shows schematically a syringe of the type using a flexible piston rod and a dosing mechanism as the one sketched in FIG. 2. The syringe comprises a housing 19 accommodating an ampoule which may be inspected through a slot shaped window 20 in the housing. On a needle receiving member at an end of the ampoule is mounted a needle hub 21 carrying an injection needle 22. A dose is set by a dose setting drum 23 and the size of the set dose is shown in a window 24. Next to the needle receiving member the housing is provided with a contact surface 25 which during the injection is held in contact with the skin to control the insertion depth of the needle. An air shot button 26 is placed in a cavity 27 in this contact surface. Operation of the air shot button 26 is transmitted to the push rod 17 shown in FIG. 2 and the pawl wheel 14 is rotated corresponding to the passage of one tooth. By positioning the air shot button in the contact surface 25 it is ensured that the air shot button is not used for injection purposes. If this security does not have a high priority, the air shot button may be placed anywhere appropriate.

Instead of working independently on the piston rod drive the air shot button may release an end stop of an injection button so that this button before a dose is set may be pressed a small distance beyond its normal end stop. An example of a air shot mechanism of this type is shown in FIG. 4. The mechanism shown in FIG. 4 corresponds to the mechanism shown in FIG. 2 and parts corresponding to the parts of FIG. 2 are given the same reference numbers. The mechanism is enlarged by a member 28 which forms and end stop for the carrier 13. The member 28 has at its end against which the end of the carrier abuts a projection 29. A further projection 30 forms an air shut button or a push rod operated by such a button. The operation of the air shot mechanism is symbolized by an arrow 31. An influence of the member 28 in the direction of the arrow 31 will displace this member to a position shown in dotted lines. Thereby the end of the member 28 will no longer form an end stop for the carrier 13 which can consequently be pressed further homeward until its end abuts the projection 29, i.e. as long as the air shot button is pressed, the carrier may be pressed past its zero point a distance which may be set to be equal to at least the length of one tooth on the carrier.

What is claimed is:

1. A syringe comprising a housing for receiving an ampoule containing a medicine, a dose setting and injection mechanism, and an air shot dispensing mechanism, wherein said dose setting and injection mechanism comprises:

a stop member supported in said housing;

a dose setting member which is supported in said housing for movement in a first direction away from said stop member and a second direction towards said stop member, wherein said dose setting member may be moved in said first direction to one of a plurality of selectable positions in order to set the amount of the dose to be dispensed;

a piston rod moveably supported in said housing for acting on a piston in an ampoule; and a unidirectional coupling mechanism between said dose setting member and said piston rod for transmitting movement of said dose setting member only in said second direction; wherein said dose setting member, after being moved in said first direction to set a dose, may be moved in said second direction until reaching said stop member, and wherein such movement of said dose setting member in said second direction causes said piston rod to move forward a distance proportional to the set dose to expel said set dose from an ampoule; and wherein said air shot dispensing mechanism comprises:

an air shot button; and an air shot coupling mechanism between said air shot button and said dose setting and injection mechanism for permitting said piston rod to move forward, by a predetermined distance, when said air shot button is actuated, without first setting a dose.

2. A syringe according to claim 1, wherein said air shot coupling mechanism couples said air shot button to said piston rod for moving said piston rod forward independently of said dose setting member.

3. A syringe according to claim 2, wherein said unidirectional coupling comprises a piston rod drive, and said air shot coupling mechanism couples the air shot button to said piston rod drive through a second unidirectional coupling such that movement of said air shot button from an initial position actuates said piston rod drive, advancing said piston rod, and wherein said second unidirectional coupling allows said air shot button, when released, to return to its initial position without influencing said piston rod.

4. A syringe according to claim 3, wherein said piston rod drive includes a member having teeth, and wherein said second unidirectional coupling comprises a pawl connected to said air shot button which engages said teeth for actuating said piston rod drive in one direction only.

5. A syringe according to claim 4, wherein said piston rod is threaded, wherein said piston rod drive includes a drive gear engaging the threads of said piston rod, and wherein said teeth for engaging said pawl are fixed relative to said drive gear.

6. A syringe according to claim 4, wherein said pawl forms a piston retraction detent to prevent movement of said piston rod drive other than in said one direction.

7. A syringe according to claim 1, wherein said air shot button is coupled to said stop member for selectively moving said stop member out of engagement with said dose setting member to permit said dose setting member to move a predetermined distance in said second direction beyond said stop member.

* * * * *